(12) United States Patent
Powell et al.

(10) Patent No.: US 9,102,584 B2
(45) Date of Patent: Aug. 11, 2015

(54) HYDROTHERMAL HYDROCATALYTIC TREATMENT OF BIOMASS USING WATER TOLERANT CATALYSTS

(71) Applicant: Shell Oil Company, Houston, TX (US)

(72) Inventors: Joseph Broun Powell, Houston, TX (US); Glenn Charles Komplin, Katy, TX (US); John Anthony Smegal, Houston, TX (US); Kimberly Ann Johnson, Richmond, TX (US)

(73) Assignee: Shell Oil Company, Houston, TX (US)

( * ) Notice: Subject to any disclaimer, the term of this patent is extended or adjusted under 35 U.S.C. 154(b) by 53 days.

(21) Appl. No.: 14/133,709

(22) Filed: Dec. 19, 2013

(65) Prior Publication Data

US 2014/0171694 A1 Jun. 19, 2014

Related U.S. Application Data

(60) Provisional application No. 61/739,348, filed on Dec. 19, 2012.

(51) Int. Cl.
*C07C 29/153* (2006.01)
*C01G 1/02* (2006.01)
*C07C 29/60* (2006.01)
(Continued)

(52) U.S. Cl.
CPC ............... *C07C 29/60* (2013.01); *B01J 21/063* (2013.01); *B01J 21/066* (2013.01); *B01J 23/86* (2013.01); *B01J 23/88* (2013.01); *B01J 23/882* (2013.01); *B01J 27/188* (2013.01); *B01J 27/19* (2013.01); *B01J 35/008* (2013.01); *B01J 37/0201* (2013.01); *B01J 37/20* (2013.01); *C10G 1/065* (2013.01); *C10G 3/46* (2013.01); *C10G 3/48* (2013.01); *C10G 3/50* (2013.01); *B01J 35/002* (2013.01); *B01J 35/1009* (2013.01); *B01J 35/1014* (2013.01); *B01J 35/1019* (2013.01); *B01J 35/1038* (2013.01); *B01J 35/1061* (2013.01); *B01J 2523/00* (2013.01); *C10G 2300/1014* (2013.01); *Y02E 50/343* (2013.01)

(58) Field of Classification Search
CPC ................................. C10G 1/02; C07C 29/153
USPC ........................................... 568/903; 585/240
See application file for complete search history.

(56) References Cited

U.S. PATENT DOCUMENTS 7,285,179 B2 10/2007 Snekkenes et al.
2011/0154721 A1 6/2011 Chheda et al.
(Continued)

FOREIGN PATENT DOCUMENTS

EP 2721125 4/2014
WO 2010/124030 * 10/2010 ............... C10G 1/10

*Primary Examiner* — Kamal Saeed
*Assistant Examiner* — Janet L Coppins

(57) ABSTRACT

A method of hydrothermal hydrocatalytic treating biomass is provided. Lignocellulosic biomass solids is provided to a hydrothermal digestion unit in the presence of a digestive solvent, and a supported hydrogenolysis catalyst containing (a) sulfur, (b) Mo or W, and (c) Co, Ni or mixture thereof, incorporated into a group 4 metal oxide support; (ii) heating the lignocellulosic biomass solids and digestive solvent in the presence of hydrogen, and the supported hydrogenolysis catalyst thereby forming a product solution containing plurality of oxygenated hydrocarbons, said catalyst retaining a crush strength of at least 50% after being subjected to an aqueous phase stability test compared with before the aqueous phase stability test or a crush strength of at least 0.25 kg after being subjected to an aqueous phase stability test.

33 Claims, 3 Drawing Sheets

(51) Int. Cl.
*B01J 21/06* (2006.01)
*C10G 1/06* (2006.01)
*C10G 3/00* (2006.01)
*B01J 37/20* (2006.01)
*B01J 23/882* (2006.01)
*B01J 27/19* (2006.01)
*B01J 37/02* (2006.01)
*B01J 23/86* (2006.01)
*B01J 23/88* (2006.01)
*B01J 27/188* (2006.01)
*B01J 35/00* (2006.01)
*B01J 35/10* (2006.01)

(56) References Cited

U.S. PATENT DOCUMENTS

| | | |
|---|---|---|
| 2011/0282115 A1 | 11/2011 | Chheda et al. |
| 2012/0152836 A1 | 6/2012 | Powell et al. |
| 2012/0317872 A1 | 12/2012 | Powell et al. |
| 2012/0317873 A1 | 12/2012 | Johnson et al. |
| 2013/0152457 A1 | 6/2013 | Powell et al. |
| 2013/0152458 A1 | 6/2013 | Powell et al. |

* cited by examiner

HYDROTHERMAL HYDROCATALYTIC TREATMENT OF BIOMASS USING WATER TOLERANT CATALYSTS

This non-provisional application claims the benefit of U.S. Patent Application No. 61/739,348, filed Dec. 19, 2012 the entire disclosure of which is hereby incorporated by reference.

FIELD OF THE INVENTION

The invention relates to the hydrothermal hydrocatalytic treatment of biomass in the production of higher hydrocarbons suitable for use in transportation fuels and industrial chemicals from biomass.

BACKGROUND OF THE INVENTION

A significant amount of attention has been placed on developing new technologies for providing energy from resources other than fossil fuels. Biomass is a resource that shows promise as a fossil fuel alternative. As opposed to fossil fuel, biomass is also renewable.

Biomass may be useful as a source of renewable fuels. One type of biomass is plant biomass. Plant biomass is the most abundant source of carbohydrate in the world due to the lignocellulosic materials composing the cell walls in higher plants. Plant cell walls are divided into two sections, primary cell walls and secondary cell walls. The primary cell wall provides structure for expanding cells and is composed of three major polysaccharides (cellulose, pectin, and hemicellulose) and one group of glycoproteins. The secondary cell wall, which is produced after the cell has finished growing, also contains polysaccharides and is strengthened through polymeric lignin covalently cross-linked to hemicellulose. Hemicellulose and pectin are typically found in abundance, but cellulose is the predominant polysaccharide and the most abundant source of carbohydrates. However, production of fuel from cellulose poses a difficult technical problem. Some of the factors for this difficulty are the physical density of lignocelluloses (like wood) that can make penetration of the biomass structure of lignocelluloses with chemicals difficult and the chemical complexity of lignocelluloses that lead to difficulty in breaking down the long chain polymeric structure of cellulose into carbohydrates that can be used to produce fuel. Another factor for this difficulty is the nitrogen compounds and sulfur compounds contained in the biomass. The nitrogen and sulfur compounds contained in the biomass can poison catalysts used in subsequent processing.

Most transportation vehicles require high power density provided by internal combustion and/or propulsion engines. These engines require clean burning fuels which are generally in liquid form or, to a lesser extent, compressed gases. Liquid fuels are more portable due to their high energy density and their ability to be pumped, which makes handling easier.

Currently, bio-based feedstocks such as biomass provide the only renewable alternative for liquid transportation fuel. Unfortunately, the progress in developing new technologies for producing liquid biofuels has been slow in developing, especially for liquid fuel products that fit within the current infrastructure. Although a variety of fuels can be produced from biomass resources, such as ethanol, methanol, and vegetable oil, and gaseous fuels, such as hydrogen and methane, these fuels require either new distribution technologies and/or combustion technologies appropriate for their characteristics. The production of some of these fuels also tends to be expensive and raise questions with respect to their net carbon savings. There is a need to directly process biomass into liquid fuels.

Processing of biomass as feeds is challenged by the need to directly couple biomass hydrolysis to release sugars, and catalytic hydrogenation/hydrogenolysis/hydrodeoxygenation of the sugar, to prevent decomposition to heavy ends (caramel, or tars). Further, nitrogen and sulfur compounds from the biomass feed can poison the hydrogenation/hydrogenolysis/hydrodeoxygenation catalysts, such as Pt/Re catalysts, and reduce the activity of the catalysts. It is further challenged by stability problems with the catalysts in aqueous phase or in organic phase or any other phases where greater than one weight percent water can be solubilized at equilibrium.

SUMMARY OF THE INVENTION

It is desirable to carry out catalytic hydrogenation/hydrogenolysis/hydrodeoxygenation of the biomass with a catalysis system that is tolerant to nitrogen and sulfur and further maintain stability and activity with minimal loss of structural integrity during the aqueous phase reactions.

In one embodiment, a method comprises: (i) providing lignocellulosic biomass solids in a hydrothermal digestion unit in the presence of a digestive solvent, and a supported hydrogenolysis catalyst containing (a) sulfur, (b) Mo or W, and (c) Co, Ni or mixture thereof, incorporated into a group 4 metal oxide support; (ii) heating the lignocellulosic biomass solids and digestive solvent in the presence of hydrogen, and the supported hydrogenolysis catalyst thereby forming a product solution containing plurality of oxygenated hydrocarbons, said catalyst retaining a crush strength of at least 50% after being subjected to an aqueous phase stability test compared with before the aqueous phase stability test.

In another embodiment, a method comprises: (i) providing lignocellulosic biomass solids in a hydrothermal digestion unit in the presence of a digestive solvent, and a supported hydrogenolysis catalyst containing (a) sulfur, (b) Mo or W, and (c) Co, Ni or mixture thereof, incorporated into a group 4 metal oxide support; (ii) heating the lignocellulosic biomass solids and digestive solvent in the presence of hydrogen, and the supported hydrogenolysis catalyst thereby forming a product solution containing a plurality of oxygenated hydrocarbons, said catalyst retaining a crush strength of at least 0.25 kg after being subjected to an aqueous phase stability test.

In another embodiment, a method comprises: (i) providing a lignocellulosic biomass solids (ii) contacting the biomass solids with a digestive solvent to form a pretreated biomass containing soluble carbohydrates; (iii) contacting the pretreated biomass with hydrogen at a temperature in the range of 180° C. to less than 300° C. in the presence of a supported hydrogenolysis catalyst containing (a) sulfur, (b) Mo or W, and (c) Co, Ni or mixture thereof, incorporated into a group 4 metal oxide support, to form a plurality of oxygenated products, said catalyst retaining a crush strength of at least 50% after being subjected to an aqueous phase stability test compared with before the aqueous phase stability test.

In yet another embodiment, a composition comprises:
(a) lignocellulosic biomass;
(b) hydrogenolysis catalyst containing (a) sulfur, (b) Mo or W, and (c) Co, Ni or mixture thereof, incorporated into a group 4 metal oxide support, said catalyst retaining a crush strength of at least 50% after being subjected to an aqueous phase stability test compared with before the aqueous phase stability test;

(c) water; and
(d) digestive solvent.

In yet another embodiment, a composition comprises:
(a) lignocellulosic biomass;
(b) hydrogenolysis catalyst comprising (a) sulfur, (b) Mo or W, and (c) Co, Ni or mixture thereof, incorporated into a group 4 metal oxide support, said catalyst having a crush strength of at least 0.25 kg after being subjected to an aqueous phase stability test;
(c) water; and
(d) digestive solvent.

The features and advantages of the invention will be apparent to those skilled in the art. While numerous changes may be made by those skilled in the art, such changes are within the spirit of the invention.

BRIEF DESCRIPTION OF THE DRAWING

This drawing illustrates certain aspects of some of the embodiments of the invention, and should not be used to limit or define the invention.

DETAILED DESCRIPTION OF THE INVENTION

Figure 1:
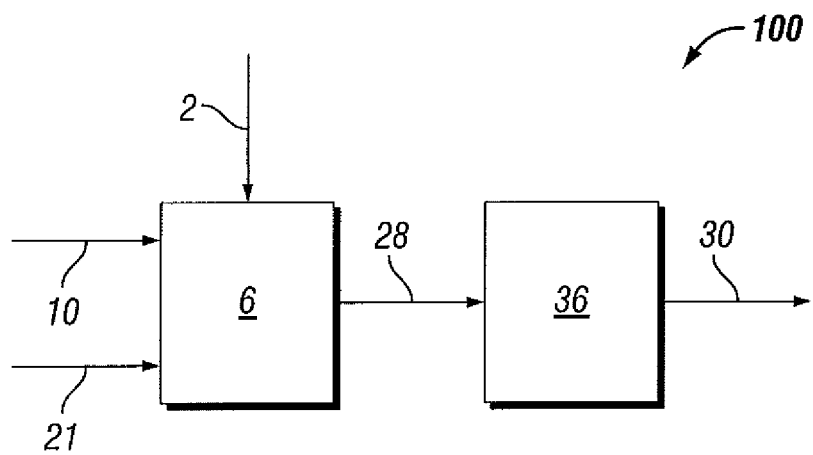
FIG. 1 is a schematically illustrated block flow diagram of an embodiment of a process 100 of this invention.

The invention relates to the hydrothermal hydrocatalytic treatment of the biomass with a catalysis system that is tolerant to nitrogen and sulfur and further maintains activity and integrity for a prolonged period with minimal loss of stability.

In one embodiment, it has been found that a supported hydrothermal hydrocatalytic catalyst (supported hydrogenolysis catalyst) containing (a) sulfur, (b) Mo or W, and (c) Co, Ni or mixture thereof, incorporated into a group 4 metal oxide support, provide a water tolerant catalyst that retains a crush strength of at least 0.25 kg, preferably at least 0.4 kg (knife edge method) after being subjected to an aqueous phase stability test.

Crush strength is defined as the resistance of formed catalysts to compressive forces. Measurements of crush strength provide an indication of the ability of the catalyst to maintain its physical integrity during handling and use. For a hydrothermal hydrocatalytic treatment of biomass, the catalyst is exposed to aqueous conditions during catalytic reactions unlike typical refining operation conducted in hydrocarbon environment. Thus, the stability of the catalyst in aqueous conditions is important to maintain catalyst life.

One measurement of (bulk) crush strength is provided in ASTM D6175. Another method is knife edge crush strength. In this method, it measures minimum crush strength regardless of its particle (or pellet) size.

In one embodiment, it has been found that supported hydrothermal hydrocatalytic catalyst (supported hydrogenolysis catalyst) containing (a) sulfur, (b) Mo or W, and (c) Co, Ni or mixture thereof, incorporated a group 4 metal oxide support, such as zirconia and titania, provide a water tolerant catalyst that retaining a crush strength of at least 50%, preferably at least 60% after being subjected to an aqueous phase stability test compared with before the aqueous phase stability test. The aqueous phase stability test is conducted by placing one part catalyst in at least 5 parts water for 1 week at 250° C. in a sealed tube and comparing the crush strength of the catalyst before and after the test.

The oxygenated hydrocarbons produced from the process are useful in the production of higher hydrocarbons suitable for use in transportation fuels and industrial chemicals from biomass. The higher hydrocarbons produced are useful in forming transportation fuels, such as synthetic gasoline, diesel fuel, and jet fuel, as well as industrial chemicals. As used herein, the term "higher hydrocarbons" refers to hydrocarbons having an oxygen to carbon ratio less than the oxygen to carbon ratio of at least one component of the biomass feedstock. As used herein the term "hydrocarbon" refers to an organic compound comprising primarily hydrogen and carbon atoms, which is also an unsubstituted hydrocarbon. In certain embodiments, the hydrocarbons of the invention also comprise heteroatoms (i.e., oxygen sulfur, phosphorus, or nitrogen) and thus the term "hydrocarbon" may also include substituted hydrocarbons. The term "soluble carbohydrates" refers to oligosaccharides and monosaccharides that are soluble in the digestive solvent and that can be used as feedstock to the hydrogenolysis reaction (e.g., pentoses and hexoses).

Processing of biomass as feeds is challenged by the need to directly couple biomass hydrolysis to release sugars, and catalytic hydrogenation/hydrogenolysis/hydrodeoxygenation of the sugar, to prevent decomposition to heavy ends (caramel, or tars). Nitrogen and sulfur compounds from the biomass feed can be poison the hydrogenation/hydrogenolysis/hydrodeoxygenation catalysts, such as Pt/Re catalysts, and reduce the activity of the catalysts. Reduced or partially reduced nitrogen or sulfur compounds such as those found in proteins and amino acids present in the biomass feed, are potential poisons for transition metal catalysts used to activate molecular hydrogen for reduction reactions. Oxidized forms of nitrogen or sulfur, in the form of nitrates or sulfates may not poison many catalysts used for hydrogen activation and reduction reactions. Biomass hydrolysis starts above 120° C. and continues through 200° C. Sulfur and nitrogen compounds can be removed by ion exchange resins (acidic) such as discussed in US publication no. US2012/0152836, that are stable to 120° C., but the base resins required for complete N, S removal cannot be used above 100° C. (weak base), or 60° C. for the strong base resins. Cycling of temperature from 60° C. ion exchange to reaction temperatures between 120-275° C. represents a substantial energy yield loss. Use of a poison tolerant catalyst in the process to enable direct coupling of biomass hydrolysis and catalytic hydrogenation/hydrogenolysis/hydrodeoxygenation of the resulting sugar is an advantage, for a biomass feed process. The methods and systems of the invention have an advantage of using a poison tolerant catalyst for the direct coupling of biomass hydrolysis and catalytic hydrogenation/hydrogenolysis/hydrodeoxygenation of the resulting sugar and other derived intermediates, with minimal loss of active metal over time.

In some embodiments, at least a portion of oxygenated hydrocarbons produced in the hydrogenolysis reaction are recycled within the process and system to at least in part from the in situ generated solvent, which is used in the biomass digestion process. This recycle saves costs in provision of a solvent that can be used to extract nitrogen, sulfur, and optionally phosphorus compounds from the biomass feedstock. Further, by controlling the degradation of carbohydrate in the hydrogenolysis process, hydrogenation reactions can be conducted along with the hydrogenolysis reaction at temperatures ranging from about 150° C. to less than about 300° C. As a result, a separate hydrogenation reaction section can optionally be avoided, and the fuel forming potential of the biomass feedstock fed to the process can be increased. This process and reaction scheme described herein also results in a capital cost savings and process operational cost savings. Advantages of specific embodiments will be described in more detail below.

In one embodiment, a method comprises: (i) providing lignocellulosic biomass solids in a hydrothermal digestion unit in the presence of a digestive solvent, and a supported hydrogenolysis catalyst containing (a) sulfur, (b) Mo or W, and (c) Co, Ni or mixture thereof, incorporated into a group 4 metal oxide support; (ii) heating the lignocellulosic biomass solids and digestive solvent in the presence of hydrogen, and supported hydrogenolysis catalyst thereby forming a product solution containing plurality of oxygenated hydrocarbons, said catalyst retaining a crush strength of at least 50% after being subjected to an aqueous phase stability test compared with before the aqueous phase stability test or at the minimum having a crush strength of at least 0.25 kg after being subjected to an aqueous phase stability test.

In another embodiment, a method comprises: (i) providing a lignocellulosic biomass solids (ii) contacting the biomass solids with a digestive solvent to form a pretreated biomass containing soluble carbohydrates; (iii) contacting the pretreated biomass with hydrogen at a temperature in the range of 180° C. to less than 300° C. in the presence of a supported hydrogenolysis catalyst containing (a) sulfur, (b) Mo or W, and (c) Co, Ni or mixture thereof, incorporated into a group 4 metal oxide support, to form a plurality of oxygenated products, said catalyst retaining a crush strength of at least 50% after being subjected to an aqueous phase stability test compared with before the aqueous phase stability test or at the minimum having a crush strength of at least 0.25 kg after being subjected to an aqueous phase stability test.

In one embodiment, buffering agent may optionally be continuously or semi-continuously or periodically added to the reaction system (or reaction mixture) to minimize active metal leaching and maintain catalyst activity. Suitable pH buffering agent for the process of the invention is a buffering agent that is capable of maintaining the pH of the reaction mixture at a desirable pH. In one embodiment, pH may be in the range of about 3 to about 10, preferably to about 4 to about 8, more preferably to about 5 to about 7. In another embodiment, it may be desirable to run the reaction system under more basic conditions. The pH buffering agent may be an inorganic salt, particularly alkali salts such as, for example, potassium hydroxide, sodium hydroxide, and potassium carbonate. Group IIA salts such as calcium in the form of oxide, hydroxide, or carbonate may be used as buffer, even if not fully soluble in the reaction medium. The pH buffering agents may include any basic compound capable of adjusting the solution pH to the target range without adversely effecting the reaction of the catalyst. Such basic compound, for example may include, but not limited to, inorganic bases (including inorganic salts) such as Group 1A or 2A oxides, hydroxides, alkoxides, carbonates, bicarbonates, mono-, di, or tri-basic phosphates, mono-, di-basic sulfates, borates, carboxylates including those of di- or tri-acids. Ammonia (including sources of ammonia) and ammonium salts, including various alkyl ammonium salts may also be used.

In some embodiments, lignocellulosic biomass (solids) being continuously or semi-continuously added to the hydrothermal digestion unit may be pressurized before being added to the hydrothermal digestion unit, particularly when the hydrothermal digestion unit is in a pressurized state. Pressurization of the cellulosic biomass solids from atmospheric pressure to a pressurized state may take place in one or more pressurization zones before addition of the cellulosic biomass solids to the hydrothermal digestion unit. Suitable pressurization zones that may be used for pressurizing and introducing lignocellulosic biomass to a pressurized hydrothermal digestion unit are described in more detail in commonly owned United States Patent Application Publications 20130152457 and 20130152458, and incorporated herein by reference in its entirety. Suitable pressurization zones described therein may include, for example, pressure vessels, pressurized screw feeders, and the like. In some embodiments, multiple pressurization zones may be connected in series to increase the pressure of the cellulosic biomass solids in a stepwise manner.

In reference to FIG. 1, in one embodiment of the invention process 100, biomass 2 is provided to digestion unit 6, that may have one or more units, containing a water tolerant catalyst, and a digestive solvent 10 (that may be recycled from the process, whereby when heated with molecular hydrogen 21 produces oxygenated hydrocarbons. The effluent product stream from the digestion unit 28 contains oxygenated hydrocarbons. The oxygenated hydrocarbons may be further processed 36 in yet another hydrogenolysis process to further produce oxygenated hydrocarbons and/or further processed to produce higher hydrocarbons 30 to form a liquid fuel. In one embodiment the digester-reactor may be configured as disclosed in a co-pending U.S. application No. 61/720,757 filed Oct. 31, 2012 which disclosure is hereby incorporated by reference.

Figure 2:
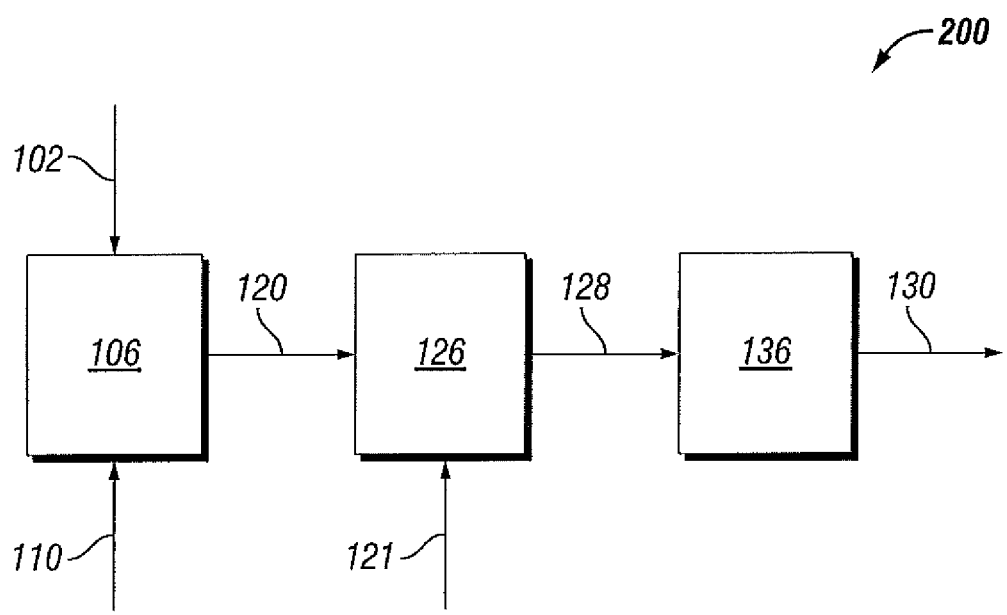
FIG. 2 is a schematically illustrated block flow diagram of an embodiment of a process 200 of this invention.

In reference to FIG. 2, in one embodiment of the invention process 200, biomass 102 is provided to digestion zone 106 that may have one or more digester(s), whereby the biomass is contacted with a digestive solvent 110. The treated biomass pulp 120 contains soluble carbohydrates and other intermediates containing sulfur compounds and nitrogen compounds from the biomass. The sulfur and nitrogen content may vary depending on the biomass source 102. At least a portion of the treated biomass 120 is catalytically reacted with hydrogen 121, in the hydrothermal hydrocatalytic treatment zone 126, in the presence of the water tolerant hydrogenolysis catalyst to produce a product stream 128 containing plurality of oxygenated hydrocarbons. At least a portion of the oxygenated hydrocarbon intermediates may be processed further 136 to produce higher hydrocarbons 130 to form a liquid fuel. The digestion zone 106 and the hydrothermal hydrocatalytic treatment zone 126 may be conducted in the same reactor or in a separate reactor. The treated biomass 120 may be optionally washed prior to contacting in the hydrogenolysis zone 126. If washed, water is most typically used as wash solvent.

Any suitable (e.g., inexpensive and/or readily available) type of lignocellulosic biomass can be used. Suitable lignocellulosic biomass can be, for example, selected from, but not limited to, forestry residues, agricultural residues, herbaceous material, municipal solid wastes, waste and recycled paper, pulp and paper mill residues, and combinations thereof. Thus, in some embodiments, the biomass can comprise, for example, corn stover, straw, bagasse, miscanthus, sorghum residue, switch grass, bamboo, water hyacinth, hardwood, hardwood chips, hardwood pulp, softwood, softwood chips, softwood pulp, and/or combination of these feedstocks. The biomass can be chosen based upon a consideration such as, but not limited to, cellulose and/or hemicelluloses content, lignin content, growing time/season, growing location/transportation cost, growing costs, harvesting costs and the like.

Prior to treatment with the digestive solvent, the untreated biomass can be washed and/or reduced in size (e.g., chopping, crushing or debarking) to a convenient size and certain quality that aids in moving the biomass or mixing and impregnating the chemicals from digestive solvent. Thus, in some embodiments, providing biomass can comprise harvesting a lignocelluloses-containing plant such as, for example, a hardwood or softwood tree. The tree can be subjected to debarking, chopping to wood chips of desirable thickness, and washing to remove any residual soil, dirt and the like.

It is recognized that washing with water prior to treatment with digestive solvent is desired, to rinse and remove simple salts such as nitrate, sulfate, and phosphate salts which otherwise may be present, and contribute to measured concentrations of nitrogen, sulfur, and phosphorus compounds present. This wash is accomplished at a temperature of less than about 60 degrees Celsius, and where hydrolysis reactions comprising digestion do not occur to a significant extent. Other nitrogen, sulfur, and phosphorus compounds are bound to the biomass and are more difficult to remove, and requiring digestion and reaction of the biomass, to effect removal. These compounds may be derived from proteins, amino acids, phospholipids, and other structures within the biomass, and may be potent catalyst poisons. The poison tolerant catalyst described herein, allows some of these more difficult to remove nitrogen and sulfur compounds to be present in subsequent processing.

In the digestion zone, the size-reduced biomass is contacted with the digestive solvent where the digestion reaction takes place. The digestive solvent must be effective to digest lignins.

In one aspect of the embodiment, the digestive solvent maybe a Kraft-like digestive solvent that contains (i) at least 0.5 wt %, preferably at least 4 wt %, to at most 20 wt %, more preferably to 10 wt %, based on the digestive solvent, of at least one alkali selected from the group consisting of sodium hydroxide, sodium carbonate, sodium sulfide, potassium hydroxide, potassium carbonate, ammonium hydroxide, and mixtures thereof, (ii) optionally, 0 to 3%, based on the digestive solvent, of anthraquinone, sodium borate and/or polysulfides; and (iii) water (as remainder of the digestive solvent). In some embodiments, the digestive solvent may have an active alkali of between 0.5% to 25%, more preferably between 10 to 20%. The term "active alkali" (AA), as used herein, is a percentage of alkali compounds combined, expressed as sodium oxide based on weight of the biomass less water content (dry solid biomass). The digestion is carried out typically at a cooking-liquor to biomass ratio in the range of 2 to 6, preferably 3 to 5. The digestion reaction is carried out at a temperature within the range of from about 60° C., preferably 100° C., to about 270° C., and a residence time within 0.25 h to 24 h. The reaction is carried out under conditions effective to provide a pretreated biomass stream containing pretreated biomass having a lignin content that is less than about 20% of the amount in the untreated biomass feed, and a chemical liquor stream containing alkali compounds and dissolved lignin and hemicellulose material.

The digestion can be carried out in a suitable vessel, for example, a pressure vessel of carbon steel or stainless steel or similar alloy. The digestion zone can be carried out in the same vessel or in a separate vessel. The cooking can be done in continuous or batch mode. Suitable pressure vessels include, but are not limited to the "PANDIA™ Digester" (Voest-Alpine Industrienlagenbau GmbH, Linz, Austria), the "DEFIBRATOR Digester" (Sunds Defibrator AB Corporation, Stockholm, Sweden), M&D (Messing & Durkee) digester (Bauer Brothers Company, Springfield, Ohio, USA) and the KAMYR Digester (Andritz Inc., Glens Falls, N.Y., USA). The digestive solvent has a pH from 10 to 14, preferably around 12 to 13 depending on the concentration of active alkali AA. The contents can be kept at a temperature within the range of from 100° C. to 230° C. for a period of time, more preferably within the range from about 130° C. to about 180° C. The period of time can be from about 0.25 to 24.0 hours, preferably from about 0.5 to about 2 hours, after which the pretreated contents of the digester are discharged. For adequate penetration, a sufficient volume of liquor is required to ensure that all the biomass surfaces are wetted. Sufficient liquor is supplied to provide the specified digestive solvent to biomass ratio. The effect of greater dilution is to decrease the concentration of active chemical and thereby reduce the reaction rate.

In a system using the digestive solvent such as a Kraft-like digestive solvent similar to those used in a Kraft pulp and paper process, the chemical liquor may be regenerated in a similar manger to a Kraft pulp and paper chemical regeneration process.

In another embodiment, an at least partially water miscible organic solvent that has partial solubility in water, preferably greater than 2 weight percent in water, may be used as digestive solvent to aid in digestion of lignin, and the nitrogen, and sulfur compounds. In one such embodiment, the digestive solvent is a water-organic solvent mixture with optional inorganic acid promoters such as HCl or sulfuric acid. Oxygenated solvents exhibiting full or partial water solubility are preferred digestive solvents. In such a process, the organic digestive solvent mixture can be, for example, methanol, ethanol, acetone, ethylene glycol, propylene glycol, triethylene glycol and tetrahydrofurfuryl alcohol. Organic acids such as acetic, oxalic, acetylsalicylic and salicylic acids can also be used as catalysts (as acid promoter) in the at least partially miscible organic solvent process. Temperatures for the digestion may range from about 130 to about 270° C., preferably from about 140 to 220° C., and contact times from 0.25 to 24 hours, preferably from about one to 4 hours. Preferably, a pressure from about 2 to 100 bar, and most typically from 5 to 50 bar, is maintained on the system to avoid boiling or flashing away of the solvent.

Optionally the pretreated biomass stream can be washed prior to hydrogenolysis zone depending on the embodiment. In the wash system, the pretreated biomass stream can be washed to remove one or more of non-cellulosic material, and non-fibrous cellulosic material prior to hydrogenolysis. The pretreated biomass stream is optionally washed with a water stream under conditions to remove at least a portion of lignin, hemicellulosic material, and salts in the pretreated biomass stream. For example, the pretreated biomass stream can be washed with water to remove dissolved substances, including degraded, but non-processable cellulose compounds, solubilized lignin, and/or any remaining alkaline chemicals such as sodium compounds that were used for cooking or produced during the cooking (or pretreatment). The washed pretreated biomass stream may contain higher solids content by further processing such as mechanical dewatering as described below.

In a preferred embodiment, the pretreated biomass stream is washed counter-currently. The wash can be at least partially carried out within the digester and/or externally with separate washers. In one embodiment of the invention process, the wash system contains more than one wash steps, for example, first washing, second washing, third washing, etc. that produces washed pretreated biomass stream from first washing, washed pretreated biomass stream from second washing, etc. operated in a counter current flow with the water, that is then sent to subsequent processes as washed pretreated biomass stream. The water is recycled through first recycled wash stream and second recycled wash stream and then to third recycled wash stream. Water recovered from the chemical liquor stream by the concentration system can be recycled as wash water to wash system. It can be appreciated that the washed steps can be conducted with any number of steps to obtain the desired washed pretreated biomass stream. Additionally, the washing may adjust the pH for subsequent steps to the desired pH for the hydrothermal hydrocatalytic treatment. The ammonium hydroxide or an ammonium hydroxide precursor may be optionally added at this step to adjust the pH to the desired pH for the hydrothermal hydrocatalytic treatment.

In one embodiment of the invention process, biomass 102 is provided to digestion zone 106 that may have one or more digestion zones and/or digesting vessels, whereby the biomass is contacted with a digestive solvent. The digestive solvent is optionally at least a portion recycled from the hydrogenolysis reaction as a recycle stream. The hydrogenolysis recycle stream can comprise a number of components including in situ generated solvents, which may be useful as digestive solvent at least in part or in entirety. The term "in situ" as used herein refers to a component that is produced within the overall process; it is not limited to a particular reactor for production or use and is therefore synonymous with an in-process generated component. The in situ generated solvents may comprise oxygenated intermediates. The digestive process to remove nitrogen, and sulfur compounds may vary within the reaction media so that a temperature gradient exists within the reaction media, allowing for nitrogen, and sulfur compounds to be extracted at a lower temperature than cellulose. For example, the reaction sequence may comprise an increasing temperature gradient from the biomass feedstock 102. The non-extractable solids may be removed from the reaction as an outlet stream. The treated biomass stream 120 is an intermediate stream that may comprise the treated biomass at least in part in the form of carbohydrates. The composition of the treated biomass stream 120 may vary and may comprise a number of different compounds. Preferably, the contained carbohydrates will have 2 to 12 carbon atoms, and even more preferably 2 to 6 carbon atoms. The carbohydrates may also have an oxygen to carbon ratio from 0.5:1 to 1:1.2. Oligomeric carbohydrates containing more than 12 carbon atoms may also be present. In one embodiment, at least a portion of the digested pulp is contacted with hydrogen in the presence of the water tolerant catalyst to produce a plurality of oxygenated hydrocarbons. In another embodiment, lignocellulosic biomass is contacted with hydrogen in the presence of digestive solvent and the water tolerant catalyst to produce a plurality of oxygenated hydrocarbons. A first portion of the oxygenated hydrocarbon (or oxygenated intermediate stream) from product stream 128 or 28 can be recycled to digestion zone 106 or hydrothermal digestion unit 6, respectively. A second portion of the oxygenated hydrocarbon (or oxygenated intermediates stream) is processed to produce higher hydrocarbons to form a liquid fuel Use of separate processing zones for steps (ii) and (iii) allows conditions to be optimized for digestion and hydrogenation or hydrogenolysis of the digested biomass components, independent from optimization of the conversion of oxygenated intermediates to monooxygenates, before feeding to step (iv) to make higher hydrocarbon fuels. A lower reaction temperature in step (iii) may be advantageous to minimize heavy ends byproduct formation, by conducting the hydrogenation and hydrogenolysis steps initially at a low temperature. This has been observed to result in an intermediates stream which is rich in diols and polyols, but essentially free of non-hydrogenated monosaccharides which otherwise would serve as heavy ends precursors. The subsequent conversion of mostly solubilized intermediates can be done efficiently at a higher temperature, where residence time is minimized to avoid the undesired continued reaction of monooxygenates to form alkane or alkene byproducts. In this manner, overall yields to desired monooxygenates may be improved, via conducting the conversion in two or more stages.

Solubilization and hydrolysis becoming complete at temperatures around 210° C., aided by organic acids (e.g., carboxylic acids) formed from partial degradation of carbohydrate components. Some lignin can be solubilized before hemicellulose, while other lignin may persist to higher temperatures. Organic in situ generated solvents, which may comprise a portion of the oxygenated intermediates, including, but not limited to, light alcohols and polyols, can assist in solubilization and extraction of lignin and other components.

At temperatures above about 120° C., carbohydrates can degrade through a series of complex self-condensation reactions to form caramelans, which are considered degradation products that are difficult to convert to fuel products. In general, some degradation reactions can be expected with aqueous reaction conditions upon application of temperature, given that water will not completely suppress oligomerization and polymerization reactions.

In certain embodiments, the hydrolysis reaction can occur at a temperature between 20° C. and 270° C. and a pressure between 1 atm and 100 atm. An enzyme may be used for hydrolysis at low temperature and pressure. In embodiments including strong acid and enzymatic hydrolysis, the hydrolysis reaction can occur at temperatures as low as ambient temperature and pressure between 1 bar (100 kPa) and 100 bar (10,100 kPa). In some embodiments, the hydrolysis reaction may comprise a hydrolysis catalyst (e.g., a metal or acid catalyst) to aid in the hydrolysis reaction. The catalyst can be any catalyst capable of effecting a hydrolysis reaction. For example, suitable catalysts can include, but are not limited to, acid catalysts, base catalysts, metal catalysts, and any combination thereof. Acid catalysts can include organic acids such as acetic, formic, levulinic acid, and any combination thereof. In an embodiment the acid catalyst may be generated in the hydrogenolysis reaction and comprise a component of the oxygenated intermediate stream.

In some embodiments, the digestive solvent may contain an in situ generated solvent. The in situ generated solvent generally comprises at least one alcohol, ketone, or polyol capable of solvating some of the sulfur compounds, and nitrogen compounds of the biomass feedstock. For example, an alcohol may be useful for solvating nitrogen, sulfur, and optionally phosphorus compounds, and in solvating lignin from a biomass feedstock for use within the process. The in situ generated solvent may also include one or more organic acids. In some embodiments, the organic acid can act as a catalyst in the removal of nitrogen and sulfur compounds by some hydrolysis of the biomass feedstock. Each in situ generated solvent component may be supplied by an external source, generated within the process, and recycled to the hydrolysis zone, or any combination thereof. For example, a portion of the oxygenated intermediates produced in the hydrogenolysis reaction may be separated in the separator stage for use as the in situ generated solvent in the hydrolysis reaction. In an embodiment, the in situ generated solvent can be separated, stored, and selectively injected into the recycle stream so as to maintain a desired concentration in the recycle stream.

Each reactor vessel preferably includes an inlet and an outlet adapted to remove the product stream from the vessel or reactor. In some embodiments, the vessel in which at least some digestion occurs may include additional outlets to allow for the removal of portions of the reactant stream. In some embodiments, the vessel in which at least some digestion occurs may include additional inlets to allow for additional solvents or additives.

The digestion may occur in any contactor suitable for solid-liquid contacting. The digestion may for example be conducted in a single or multiple vessels, with biomass solids either fully immersed in liquid digestive solvent, or contacted with solvent in a trickle bed or pile digestion mode. As a further example, the digestion step may occur in a continuous multizone contactor as described in U.S. Pat. No. 7,285,179 (Snekkenes et al., "Continuous Digester for Cellulose Pulp including Method and Recirculation System for such Digester"), which disclosure is hereby incorporated by reference. Alternately, the digestion may occur in a fluidized bed or stirred contactor, with suspended solids. The digestion may be conducted batch wise, in the same vessel used for pre-wash, post wash, and/or subsequent reaction steps.

The relative composition of the various carbohydrate components in the treated biomass stream affects the formation of undesirable by-products such as tars or heavy ends in the hydrogenolysis reaction. In particular, a low concentration of carbohydrates present as reducing sugars, or containing free aldehyde groups, in the treated biomass stream can minimize the formation of unwanted by-products. In preferred embodiments, it is desirable to have a concentration of no more than about 5 wt %, based upon total liquid, of readily degradable carbohydrates in monomeric form, or heavy end precursors in the treated biomass, while maintaining a total organic intermediates concentration, which can include the oxygenated intermediates (e.g., mono-oxygenates, diols, and/or polyols) derived from the carbohydrates, as high as possible, via use of concerted reaction or rapid recycle of the liquid between the digestion zone, and a catalytic reaction zone converting the solubilized carbohydrates to oxygenated intermediates.

For any of the configurations, a substantial portion of lignin is removed with solvent from digesting step. In one configuration, the remaining lignin, if present, can be removed upon cooling or partial separation of oxygenates from hydrogenolysis product stream, to comprise a precipitated solids stream. Optionally, the precipitated solids stream containing lignin may be formed by cooling the digested solids stream prior to hydrogenolysis reaction. In yet another configuration, the lignin which is not removed with digestion solvent is passed into step (iv), where it may be precipitated upon vaporization or separation of hydrogenolysis product stream, during processing to produce a higher hydrocarbon stream.

The treated biomass stream 120 may comprise C5 and C6 carbohydrates that can be reacted in the hydrogenolysis reaction. For embodiments comprising hydrogenolysis, oxygenated intermediates such as sugar alcohols, sugar polyols, carboxylic acids, ketones, and/or furans can be converted to fuels in a further processing reaction. The hydrogenolysis reaction comprises hydrogen and a hydrogenolysis catalyst to aid in the reactions taking place. The various reactions can result in the formation of one or more oxygenated hydrocarbon (or oxygenated intermediate streams) 128.

One suitable method for performing hydrogenolysis of carbohydrate-containing biomass includes contacting a carbohydrate or stable hydroxyl intermediate with hydrogen or hydrogen mixed with a suitable gas and a hydrogenolysis catalyst in a hydrogenolysis reaction under conditions effective to form a reaction product comprising smaller molecules or polyols. Most typically, hydrogen is dissolved in the liquid mixture of carbohydrate, which is in contact with the catalyst under conditions to provide catalytic reaction. At least a portion of the carbohydrate feed is contacted directly with hydrogen in the presence of the hydrogenolysis catalyst. By the term "directly", the reaction is carried out on at least a portion of the carbohydrate without necessary stepwise first converting all of the carbohydrates into a stable hydroxyl intermediate. As used herein, the term "smaller molecules or polyols" includes any molecule that has a lower molecular weight, which can include a smaller number of carbon atoms or oxygen atoms than the starting carbohydrate. In an embodiment, the reaction products include smaller molecules that include polyols and alcohols. This aspect of hydrogenolysis entails breaking of carbon-carbon bonds, where hydrogen is supplied to satisfy bonding requirements for the resulting smaller molecules, as shown for the example:

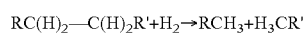

where R and R' are any organic moieties.

In an embodiment, a carbohydrate (e.g., a 5 and/or 6 carbon carbohydrate molecule) can be converted to stable hydroxyl intermediates comprising propylene glycol, ethylene glycol, and glycerol using a hydrogenolysis reaction in the presence of a hydrogenolysis catalyst.

The water stable hydrogenolysis catalyst include a group 4 metal oxide support material, preferably a stabilized group 4 metal oxide, that has incorporated therein or is loaded with a metal component, which is or can be converted to a metal compound that has activity towards the catalytic hydrogenolysis of soluble carbohydrates. The group 4 metal oxide material may be zirconia or titania. Preferably, the group 4 metal oxide is in a stabilized form. Zirconia is produced by calcining zirconium compounds. By adding small percentages of dopant such as, for example, magnesia, yttria, hafnia, ceria, the zirconia are stabilized (by elimination of phase changes), and the resulting material has superior thermal, mechanical, and/or electrical properties. Titania can be produced or purified from naturally occurring mineral ore. By adding small percentages of dopant such as, for example, zirconia, silica, alumina, niobia, the titania are stabilized, and the resulting material has superior thermal, mechanical, and/or electrical properties. Zirconia and titania are available commercially from various suppliers such as BASF, Sakai Chemical Industry Co., ltd., and Saint-Gobain Norpro.

Figure 4:
FIG. 4 is a photograph of a cross section of the zirconia supported catalyst of example 4.

In some embodiments, the metal loading per unit volume of the catalyst is like an "egg shell" where the metal is loaded towards the outer part of the catalyst compared to the interior of the catalyst as can be seen in the photograph of FIG. 4. It is believed that such loading allows catalyst to be more active compared to an equivalently loaded catalyst with the metal loading throughout the catalyst. For an egg shell like loaded catalyst, the metal loading per unit volume of the catalyst comprising the outer 30% of the catalyst volume, is more than 25% greater than the metal loading averaged over the entire catalyst volume and mass. The outer most volume is the volume farthest from the particle center or from the center axis of longest (longitudinal) dimension.

In the preparation of the hydrogenolysis catalyst, the metal component of the catalyst composition may be incorporated into the support material by any suitable method or means that provides the support material that is loaded with an active metal precursor, thus, the composition includes the support material and a metal component. One method of incorporating the metal component into the support material, includes, for example, co-mulling the support material with the active metal or metal precursor to yield a co-mulled mixture of the two components. Or, another method includes the co-precipitation of the support material and metal component to form a co-precipitated mixture of the support material and metal component. Or, in a preferred method, the support material is impregnated with the metal component using any of the known impregnation methods such as incipient wetness to incorporate the metal component into the support material.

When using the impregnation method to incorporate the metal component into the support material, it is preferred for the support material to be formed into a shaped particle comprising an group 4 metal oxide material and thereafter loaded with an active metal precursor, preferably, by the impregnation of the shaped particle with an aqueous solution of a metal salt to give the support material containing a metal of a metal salt solution. To form the shaped particle, the group 4 metal oxide material, which preferably is in powder form, is mixed with water and, if desired or needed, a peptizing agent and/or a binder to form a mixture that can be shaped into an agglomerate. It is desirable for the mixture to be in the form of an extrudable paste suitable for extrusion into extrudate particles, which may be of various shapes such as cylinders, trilobes, etc. and nominal sizes such as $\frac{1}{16}$", $\frac{1}{8}$", $\frac{3}{16}$", etc. The support material of the inventive composition, thus, preferably, is a shaped particle comprising an group 4 metal oxide material. The group 4 metal oxide based water tolerant catalyst is preferably heated to at least 400° C. The water tolerant catalyst may also be in a smaller particle form ("catalyst fines") rather than pellets for use as a slurry catalyst.

The water tolerant catalyst may have a surface area (determined by the BET method employing $N_2$, ASTM test method D 3037) that is in the range of from about 1 $m^2/g$ to about 500 $m^2/g$, preferably from about 1 $m^2/g$ to about 250 $m^2/g$.

In one embodiment, the group 4 metal oxide support is impregnated in one or more impregnation steps with a metal component using one or more aqueous solutions containing at least one metal salt wherein the metal compound of the metal salt solution is an active metal or active metal precursor. The metal elements are (a) molybdenum (Mo) and (b) cobalt (Co) and/or nickel (Ni). phosphorus (P) can also be a desired component. For Co and Ni, the metal salts include metal acetates, formates, citrates, oxides, hydroxides, carbonates, nitrates, sulfates, and two or more thereof. The preferred metal salts are metal nitrates, for example, such as nitrates of nickel or cobalt, or both. For Mo, the metal salts include metal oxides or sulfides. Preferred are salts containing the Mo and ammonium ion, such as ammonium heptamolybdate and ammonium dimolybdate.

Phosphorus is an additive that may be incorporated in these catalysts. Phosphorus may be added to increase the solubility of the molybdenum and to allow stable solutions of cobalt and/or nickel with the molybdenum to be formed for impregnation. Without wishing to be bound by theory, it is thought that phosphorus may also promote hydrogenation and hydrodenitrogenation (HDN). The ability to promote HDN is an important one since nitrogen compounds are known inhibitors of the HDS reaction. The addition of phosphorus to these catalysts may increase the HDN activity and therefore increases the HDS activity as a result of removal of the nitrogen inhibitors from the reaction medium. The ability of phosphorus to also promote hydrogenation is also advantageous for HDS since some of the difficult, sterically hindered sulfur molecules are mainly desulfurized via an indirect mechanistic pathway that goes through an initial hydrogenation of the aromatic rings in these molecules. The promotion of the hydrogentation activity of these catalysts by phosphorus increases the desulfurization of these types of sulfur containing molecules. The phosphorus content of the finished catalyst is typically in a range from 0.1 to 5.0 wt %.

The concentration of the metal compounds in the impregnation solution is selected so as to provide the desired metal content in the final composition of the hydrogenolysis catalyst taking into consideration the pore volume of the support material into which the aqueous solution is to be impregnated. Typically, the concentration of metal compound in the impregnation solution is in the range of from 0.01 to 100 moles per liter.

Cobalt, nickel, or combination thereof can be present in the support material having a metal component incorporated therein in an amount in the range of from about 0.5 wt. % to about 20 wt. %, preferably from about 1 wt. % to about 15 wt. %, and, most preferably, from about 1 wt. % to about 12 wt. %, based on metals components (b) and (c) as metal oxide form; and the molybdenum can be present in the support material having a metal component incorporated therein in an amount in the range of from about 1 wt. % to about 50 wt. %, preferably from about 2 wt. % to about 40 wt. %, and, most preferably, from about 2 wt. % to about 12 wt. %, based on metals components (b) and (c) as metal oxide form. The above-referenced weight percents for the metal components are based on the dry support material and the metal component as the element (change "element" to "metal oxide form") regardless of the actual form of the metal component.

The metal loaded catalyst may be sulfided prior to its loading into a reactor vessel or system for its use as hydrogenolysis catalyst or may be sulfided, in situ, in a gas phase or liquid phase activation procedure. In one embodiment, the liquid soluble carbohydrate feedstock can be contacted with a sulfur-containing compound, which can be hydrogen sulfide or a compound that is decomposable into hydrogen sulfide, under the contacting conditions of the invention. Examples of such decomposable compounds include mercaptans, $CS_2$, thiophenes, dimethyl sulfide (DMS), dimethyl sulfoxide (DMSO), sodium hydrogen sulfide, and dimethyl disulfide (DMDS). Also, preferably, the sulfiding is accomplished by contacting the hydrogen treated composition, under suitable sulfurization treatment conditions, with a suitable feedsource that contains a concentration of a sulfur compound. The sulfur compound of the hydrocarbon feedstock can be an organic sulfur compound, particularly, one that is derived from the biomass feedstock or other sulfur containing amino-acids such as cysteine.

Suitable sulfurization treatment conditions are those which provide for the conversion of the active metal components of the precursor hydrogenolysis catalyst to their sulfided form. Typically, the sulfiding temperature at which the precursor hydrogenolysis catalyst is contacted with the sulfur compound is in the range of from about 150° C. to about 450° C., preferably, from about 175° C. to about 425° C., and, most preferably, from about 200° C. to about 400° C.

When using a soluble carbohydrate feedstock that is to be treated using the catalyst to sulfide, the sulfurization conditions can be the same as the process conditions under which the hydrogenolysis is performed. The sulfiding pressure generally can be in the range of from about 1 bar to about 70 bar, preferably, from about 1.5 bar to about 55 bar, and, most preferably, from about 2 bar to about 35 bar. The resulting active catalyst typically has incorporated therein sulfur content in an amount in the range of from about 0.1 wt. % to about 40 wt. %, preferably from about 1 wt. % to about 30 wt. %, and, most preferably, from about 3 wt. % to about 24 wt. %, based on metals components (b) and (c) as metal oxide form.

The conditions for which to carry out the hydrogenolysis reaction will vary based on the type of biomass starting material and the desired products (e.g. gasoline or diesel). One of ordinary skill in the art, with the benefit of this disclosure, will recognize the appropriate conditions to use to carry out the reaction. In general, the hydrogenolysis reaction is conducted at temperatures in the range of 110° C. to 300° C., and preferably of 170° C. to less than 300° C., and most preferably of 180° C. to 290° C.

It was found that supplying the buffering agent to the hydrogenolysis reaction mixture during the course of the reaction may prolong catalyst life.

In an embodiment, the hydrogenolysis reaction is conducted at pressures in a range of 0.2 to 200 bar (20 to 20,000 kPa), and preferably in a range of 20 to 140 bar (2000 kPa to 14000 kPa), and even more preferably in the range of 50 and 110 bar (5000 to 11000 kPa).

The hydrogen used in the hydrogenolysis reaction of the current invention can include external hydrogen, recycled hydrogen, in situ generated hydrogen, and any combination thereof.

In an embodiment, the use of a hydrogenolysis reaction may produce less carbon dioxide and a greater amount of polyols than a reaction that results in reforming of the reactants. For example, reforming can be illustrated by formation of isopropanol (i.e., IPA, or 2-propanol) from sorbitol:

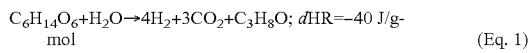

$C_6H_{14}O_6+H_2O \rightarrow 4H_2+3CO_2+C_3H_8O; dHR=-40$ J/g-mol (Eq. 1)

Alternately, in the presence of hydrogen, polyols and mono-oxygenates such as IPA can be formed by hydrogenolysis, where hydrogen is consumed rather than produced:

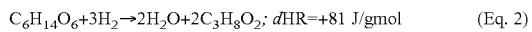

$C_6H_{14}O_6+3H_2 \rightarrow 2H_2O+2C_3H_8O_2; dHR=+81$ J/gmol (Eq. 2)

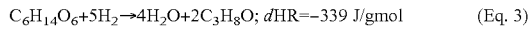

$C_6H_{14}O_6+5H_2 \rightarrow 4H_2O+2C_3H_8O; dHR=-339$ J/gmol (Eq. 3)

As a result of the differences in the reaction conditions (e.g., presence of hydrogen), the products of the hydrogenolysis reaction may comprise greater than 25% by mole, or alternatively, greater than 30% by mole of polyols, which may result in a greater conversion in a subsequent processing reaction. In addition, the use of a hydrolysis reaction rather than a reaction running at reforming conditions may result in less than 20% by mole, or alternatively less than 30% by mole carbon dioxide production. As used herein, "oxygenated intermediates" generically refers to hydrocarbon compounds having one or more carbon atoms and between one and three oxygen atoms (referred to herein as C1+O1-3 hydrocarbons), such as polyols and smaller molecules (e.g., one or more polyols, alcohols, ketones, or any other hydrocarbon having at least one oxygen atom).

In an embodiment, hydrogenolysis is conducted under neutral or acidic conditions, as needed to accelerate hydrolysis reactions in addition to the hydrogenolysis. Hydrolysis of oligomeric carbohydrates may be combined with hydrogenation to produce sugar alcohols, which can undergo hydrogenolysis.

A second aspect of hydrogenolysis entails the breaking of —OH bonds such as:

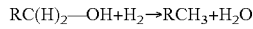

$RC(H)_2-OH+H_2 \rightarrow RCH_3+H_2O$

This reaction is also called "hydrodeoxygenation", and may occur in parallel with C—C bond breaking hydrogenolysis. Diols may be converted to mono-oxygenates via this reaction. As reaction severity is increased by increases in temperature or contact time with catalyst, the concentration of polyols and diols relative to mono-oxygenates will diminish, as a result of this reaction. Selectivity for C—C vs. C—OH bond hydrogenolysis will vary with catalyst type and formulation. Full de-oxygenation to alkanes can also occur, but is generally undesirable if the intent is to produce monoxygenates or diols and polyols which can be condensed or oligomerized to higher molecular weight fuels, in a subsequent processing step. Typically, it is desirable to send only mono-oxygenates or diols to subsequent processing steps, as higher polyols can lead to excessive coke formation on condensation or oligomerization catalysts, while alkanes are essentially unreactive and cannot be combined to produce higher molecular weight fuels.

Thus, in the reaction zone the reaction mixture may contain:

(i) lignocellulosic biomass;
(ii) a water tolerant hydrogenolysis catalyst containing (a) sulfur, (b) Mo or W, and (c) Co, Ni or mixture thereof, incorporated into group 4 metal oxide support, said catalyst retaining a crush strength of at least 50% after being subjected to an aqueous phase stability test compared with before the aqueous phase stability test or having a crush strength of at least 0.25 kg after being subjected to an aqueous phase stability test;
(iii) water; and
(iv) digestive solvent.

In some embodiment, the catalyst may further comprise (d) phosphorus.

In an embodiment of the invention, the pretreated biomass containing carbohydrates may be converted into an stable hydroxyl intermediate comprising the corresponding alcohol derivative through a hydrogenolysis reaction in addition to an optional hydrogenation reaction in a suitable reaction vessel (such as hydrogenation reaction as described in co-pending patent application publication nos. US20110154721 and US20110282115 which disclosures are hereby incorporated by reference).

The oxygenated intermediate stream 28 or 128 may then pass from the hydrogenolysis system to a further processing stage. In some embodiments, optional separation stage includes elements that allow for the separation of the oxygenated hydrocarbons into different components. In some embodiments of the present invention, the separation stage can receive the oxygenated intermediate stream 28 or 128 from the hydrogenolysis reaction and separate the various components into two or more streams. For example, a suitable separator may include, but is not limited to, a phase separator, stripping column, extractor, filter, or distillation column. In some embodiments, a separator is installed prior to a processing reaction to favor production of higher hydrocarbons by separating the higher polyols from the oxygenated intermediates. In such an embodiment, the higher polyols can be recycled back through to the hydrogenolysis reaction, while the other oxygenated intermediates are passed to the processing reaction. In addition, an outlet stream from the separation stage containing a portion of the oxygenated intermediates may act as in situ generated digestive solvent when recycled to the digester 106. In one embodiment, the separation stage can also be used to remove some or all of the lignin from the oxygenated intermediate stream. The lignin may be passed out of the separation stage as a separate stream, for example as output stream.

In an embodiment, the processing reaction may comprise a condensation reaction to produce a fuel blend. In an embodiment, the higher hydrocarbons may be part of a fuel blend for use as a transportation fuel. In such an embodiment, condensation of the oxygenated intermediates occurs in the presence of a catalyst capable of forming higher hydrocarbons. While not intending to be limited by theory, it is believed that the production of higher hydrocarbons proceeds through a stepwise addition reaction including the formation of carbon-carbon bond. The resulting reaction products include any number of compounds, as described in more detail below.

Referring to FIGS. 1 and 2, in some embodiments, an outlet stream 28 or 128 containing at least a portion of the oxygenated intermediates can pass to a processing reaction or processing reactions (36 or 136). Suitable processing reactions may comprise a variety of catalysts for condensing one or more oxygenated intermediates to higher hydrocarbons, defined as hydrocarbons containing more carbons than the oxygenated intermediate precursors. The higher hydrocarbons may comprise a fuel product. The fuel products produced by the processing reactions represent the product stream from the overall process at higher hydrocarbon stream. In an embodiment, the oxygen to carbon ratio of the higher hydrocarbons produced through the processing reactions is less than 0.5, alternatively less than 0.4, or preferably less than 0.3.

The oxygenated intermediates can be processed to produce a fuel blend in one or more processing reactions. In an embodiment, a condensation reaction can be used along with other reactions to generate a fuel blend and may be catalyzed by a catalyst comprising acid or basic functional sites, or both. In general, without being limited to any particular theory, it is believed that the basic condensation reactions generally consist of a series of steps involving: (1) an optional dehydrogenation reaction; (2) an optional dehydration reaction that may be acid catalyzed; (3) an aldol condensation reaction; (4) an optional ketonization reaction; (5) an optional furanic ring opening reaction; (6) hydrogenation of the resulting condensation products to form a C4+ hydrocarbon; and (7) any combination thereof. Acid catalyzed condensations may similarly entail optional hydrogenation or dehydrogenation reactions, dehydration, and oligomerization reactions. Additional polishing reactions may also be used to conform the product to a specific fuel standard, including reactions conducted in the presence of hydrogen and a hydrogenation catalyst to remove functional groups from final fuel product. A catalyst comprising a basic functional site, both an acid and a basic functional site, and optionally comprising a metal function, may be used to effect the condensation reaction.

In an embodiment, the aldol condensation reaction may be used to produce a fuel blend meeting the requirements for a diesel fuel or jet fuel. In an embodiment of the present invention, the fuel yield of the current process may be greater than other bio-based feedstock conversion processes. Without wishing to be limited by theory, it is believed that the water tolerant catalyst used in the process increases catalyst stability and prolongs such catalyst life.

To facilitate a better understanding of the present invention, the following examples of certain aspects of some embodiments are given. In no way should the following examples be read to limit, or define, the entire scope of the invention.

ILLUSTRATIVE EMBODIMENTS

Aqueous Phase Stability Test and Crush Strength

Three catalyst extricate samples were subjected to an Aqueous Phase Stability test ("APS test") entailing treatment of 0.25 to 0.50 grams of catalyst in 10-12 grams of deionized water in a sealed metal tube at 250° C., for 96-98 hours. After cooling, tubes were opened and catalyst extrudates dried to remove surface moisture, and subjected to lateral knife blade cutting test to assess crush strength at the end of the stability test, relative to fresh untreated catalyst. Knife blade lateral cutting measurements were performed on a precision balance, with use of a 0.91 mm blade.

EXAMPLES

Example 1

Loss of Conversion Upon Loss of Crush Resistance in Commercial Scale Reactor

A catalytic trickle bed reactor was charged with 15,300 kg of silica-supported 1/16 inch nickel extrudate hydrogenation catalyst, and operated for 3.5 months with a liquid feed of 152 kg/hr of greater than 70 wt % water, under a hydrogen pressure of 100 bar.

Temperature was increased from 60 to 125° C., to accommodate decreasing activity. At the end of life, pressure drop across the trickle bed had increased 7-fold, and apparent activity had diminished to less than 10% of original activity. Analysis of catalyst withdrawn from the bed indicated a knife-blade lateral crush strength of less than 0.25 kg for the 1/16-inch particles, or less than 1/3 of the initial crush strength, with many catalyst fines observed. This example indicates that loss of crush strength resistance upon subjecting a conventional silica- or alumina-supported catalyst to aqueous-rich feeds at elevated temperatures to obtain an average pellet crush strength below 0.25 kg leads to poor conversion in trickle bed operation, due to channeling of liquid through the collapsed catalyst bed.

Example 2

Preparation of a Water Stable Zirconia Based Catalyst

A solution of molybdenum, cobalt and phosphorus was prepared by heating a mixture of DI water (30 ml), $MoO_3$ (8.91 g), $CoCO_3$ (2.85 g) and $H_3PO_4$ (2.04 g of 85% conc) to near boiling. Heating was continued to remove excess water and bring the final solution volume to 31 ml. After cooling this solution was impregnated onto 100 g of 1.6 mm cylindrical zirconia extrudate from Saint-Gobain Norpro (Type SZ 31163, SA=50 m²/g; MPD=196 Angstroms) having a dry water pore volume of 0.31 cc/g. The impregnated catalyst is dried at 123° C. for 3 hours and then calcined at 482° C. for one hour. The metal loading on an oxide basis was 5 wt % Mo and 1.25 wt % Co.

Example 3A

Figure 3:
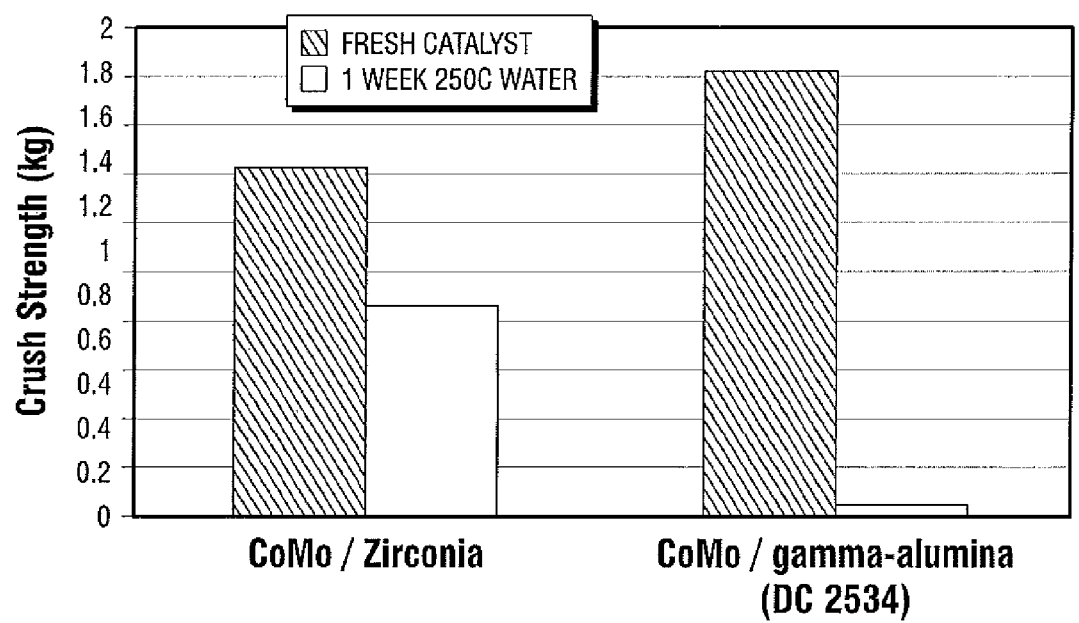
FIG. 3 is a plot of catalyst crush strength (kg) of the fresh catalyst and after one week in water at 250° C. for a zirconia support catalyst and gamma alumina support catalyst.

Crush Strength of the Water Tolerant Catalyst 0.405 grams of the zirconia based water stable catalyst of Example 2 as 1/16-inch extrudate were contacted with 11.0 grams of deionized water in the APS test. A final pH of 4.02 was measured. Initial average crush strength of 1.43 kg, diminished to 0.87 kg at the end of the APS test, which corresponds to retention of 61% of the original fresh catalyst crush resistance. FIG. 3 is a plot of the crush strength before and after the APS test.

Example 3B

Crush Strength of a Gamma Alumina Based Catalyst 0.36 grams of a commercially available cobalt molybdate catalyst on gamma alumina support (DC-2534 obtained from Criterion Catalyst & Technologies L.P, containing 1-10% cobalt oxide and molybdenum trioxide (up to 30 wt %) on gamma alumina support, and less than 2% nickel)) were contacted with 11.03 grams of deionized water for the Aqueous Phase Stability test at 250° C. An initial average crush strength of 1.82 kg was measured, which deteriorated to only 0.06 kg at the end of the APS crush test, corresponding to retention of only 3% of initial crush resistance. FIG. 3 is a plot of the crush strength before and after the APS test.

Example 4

Sulfiding of the Water Tolerant Catalyst

One gram samples of catalyst from Example 2 was added to 3.0 grams of dimethylsulfoxide (DMSO) in an autoclave reactor (Parr Instruments). The reactor was pressurized with 600 PSIG $H_2$, then the temperature was slowly ramped to 235° C. over 1 hour, with hold for 1 hour, followed by a ramp to 275° C. over 1 hour with hold for one hour, and finally with a one hour ramp to 325° C., with hold for 2 hours. The reactor was then cooled, and purged with nitrogen through caustic scrubber to remove residual sulfur compounds including hydrogen sulfide. Sulfided catalyst was collected by filtration and transferred to the dry box. A catalyst sample was cut to show cross section of the water tolerant catalyst to confirm the "egg shell" loading of the metal onto the catalyst as seen in FIG. 4.

Example 5

Catalytic Activity of the Water Tolerant Catalyst 75-milliliter Parr5000 reactors were charged with 5 grams of ethanol and 15 grams of deionized water solvent, together with 0.4 grams of glycerol a reactant. To this mixture, 0.30 grams of catalyst were added, together with 0.05 grams of sodium carbonate buffer. Reactors were pressured to 52 bar with hydrogen, and heated to 240° C. for 5 hours, before cooling to sample for analysis.

Analysis by gas chromatography using a 60-m×0.32 mm ID DB-5 column of 1 micrometer thickness, with 50:1 split ratio, 2 ml/min helium flow, and column oven at 40° C. for 8 minutes, followed by ramp to 285° C. at 10° C./min, and a hold time of 53.5 minutes. The injector temperature was set at 250° C., and the detector temperature was set at 300° C.

The sulfided zirconia supported catalyst from Example 4 was tested, and yielded a rate of 12.11/h/wt-fraction catalyst, despite an assessed loading of only 0.81 wt % cobalt and 0.71 wt % molybdenum.

This result demonstrates that good activity and water stability exceeding minimum desired requirement for the Aqueous Phase Stability test can be obtained from catalysts prepared via sulfiding of zirconia supported cobalt molybdate catalyst.

We claim:

1. A method comprising: (i) providing lignocellulosic biomass solids in a hydrothermal digestion unit in the presence of a digestive solvent, and a supported hydrogenolysis catalyst containing (a) sulfur, (b) Mo or W, and (c) Co, Ni or mixture thereof, incorporated into a group 4 metal oxide support; (ii) heating the lignocellulosic biomass solids and digestive solvent in the presence of hydrogen, and supported hydrogenolysis catalyst thereby forming a product solution containing plurality of oxygenated hydrocarbons, said catalyst retaining a crush strength of at least 50% after being subjected to an aqueous phase stability test compared with before the aqueous phase stability test.

2. The method of claim 1 wherein the lignocellulosic biomass solids is heated to a temperature in the range of 180° C. to less than 300° C.

3. The method of claim 1 wherein the catalyst retains aqueous phase stability of at least 60% after being subjected to an aqueous phase stability test.

4. The method of claim 1 wherein the group 4 metal oxide support is a stabilized form.

5. The method of claim 1 wherein the group 4 metal oxide support is zirconia.

6. The method of claim 1 wherein the group 4 metal oxide support is titania.

7. The method of claim 1 wherein the metal loading per unit volume of the catalyst comprising the outer 30% of the catalyst volume, is more than 25% greater than the metal loading averaged over the entire catalyst volume and mass.

8. The method of claim 1 wherein at least a portion of the digestive solvent is comprised of the oxygenated hydrocarbons from the product solution.

9. A method comprising: (i) providing a lignocellulosic biomass solids (ii) contacting the biomass solids with a digestive solvent to form a pretreated biomass containing soluble carbohydrates; (iii) contacting the pretreated biomass with hydrogen at a temperature in the range of 180° C. to less than 300° C. in the presence of a supported hydrogenolysis catalyst containing (a) sulfur, (b) Mo or W, and (c) Co, Ni or mixture thereof, incorporated into a group 4 metal oxide support, to form a plurality of oxygenated products, said catalyst retaining a crush strength of at least 50% after being subjected to an aqueous phase stability test compared with before the aqueous phase stability test.

10. The method of claim 9 wherein the catalyst retains a crush strength of at least 60% after being subjected to an aqueous phase stability test.

11. The method of claim 9 wherein the group 4 metal oxide support is a stabilized form.

12. The method of claim 9 wherein the group 4 metal oxide support is zirconia.

13. The method of claim 9 wherein the group 4 metal oxide support is titania.

14. The method of claim 9 wherein the metal loading per unit volume of the catalyst comprising the outer 30% of the catalyst volume, is more than 25% greater than the metal loading averaged over the entire catalyst volume and mass.

15. The method of claim 10 wherein at least a portion of the digestive solvent is comprised of the oxygenated hydrocarbons from the product solution.

16. A method comprising: (i) providing lignocellulosic biomass solids in a hydrothermal digestion unit in the presence of a digestive solvent, and a supported hydrogenolysis catalyst containing (a) sulfur, (b) Mo or W, and (c) Co, Ni or mixture thereof, incorporated into a group 4 metal oxide support; (ii) heating the lignocellulosic biomass solids and digestive solvent in the presence of hydrogen, and supported hydrogenolysis catalyst thereby forming a product solution containing plurality of oxygenated hydrocarbons, said catalyst having a crush strength of at least 0.25 kg after being subjected to an aqueous phase stability test.

17. The method of claim 16 wherein the lignocellulosic biomass solids is heated to a temperature in the range of 180° C. to less than 300° C.

18. The method of claim 16 wherein the catalyst having a crush strength of at least 0.4 kg.

19. The method of claim 16 wherein the group 4 metal oxide support is a stabilized form.

20. The method of claim 16 wherein the group 4 metal oxide support is zirconia.

21. The method of claim 16 wherein the group 4 metal oxide support is titania.

22. The method of claim 16 wherein the metal loading per unit volume of the catalyst comprising the outer 30% of the catalyst volume, is more than 25% greater than the metal loading averaged over the entire catalyst volume and mass.

23. The method of claim 16 wherein at least a portion of the digestive solvent is comprised of the oxygenated hydrocarbons from the product solution.

24. A composition comprising:
  (a) lignocellulosic biomass;
  (b) hydrogenolysis catalyst comprising (a) sulfur, (b) Mo or W, and (c) Co, Ni or mixture thereof, incorporated into a group 4 metal oxide support, said catalyst retaining a crush strength of at least 50% after being subjected to an aqueous phase stability test compared with before the aqueous phase stability test;
  (c) water; and
  (d) digestive solvent.

25. The composition of claim 24 wherein the group 4 metal oxide support is a stabilized form.

26. The composition of claim 24 wherein the group 4 metal oxide support is zirconia.

27. The composition of claim 24 wherein the group 4 metal oxide support is titania.

28. The composition of claim 24 wherein the metal loading per unit volume of the catalyst comprising the outer 30% of the catalyst volume, is more than 25% greater than the metal loading averaged over the entire catalyst volume and mass.

29. A composition comprising:
  (a) lignocellulosic biomass;
  (b) hydrogenolysis catalyst comprising (a) sulfur, (b) Mo or W, and (c) Co, Ni or mixture thereof, incorporated into a group 4 metal oxide support, said catalyst having a crush strength of at least 0.25 kg after being subjected to an aqueous phase stability test;
  (c) water; and
  (d) digestive solvent.

30. The composition of claim 29 wherein the group 4 metal oxide support is a stabilized form.

31. The composition of claim 29 wherein the group 4 metal oxide support is zirconia.

32. The composition of claim 29 wherein the group 4 metal oxide support is titania.

33. The composition of claim 29 wherein the metal loading per unit volume of the catalyst comprising the outer 30% of the catalyst volume, is more than 25% greater than the metal loading averaged over the entire catalyst volume and mass.

* * * * *